(12) United States Patent
Weiler et al.

(10) Patent No.: US 8,097,716 B2
(45) Date of Patent: Jan. 17, 2012

(54) INTERFERING RNA DUPLEX HAVING BLUNT-ENDS AND 3'-MODIFICATIONS

(75) Inventors: Jan Weiler, Lorrach-Haagen (DE); Jonathan Hall, Dornach (CH); Jean-Charles Bologna, Nimes (FR); Francois Jean-Charles Natt, Aesch (CH); Robert Haner, Uettligen (CH)

(73) Assignee: Novartis AG, Basel (CH)

( * ) Notice: Subject to any disclaimer, the term of this patent is extended or adjusted under 35 U.S.C. 154(b) by 305 days.

(21) Appl. No.: 12/338,601

(22) Filed: Dec. 18, 2008

(65) Prior Publication Data
US 2009/0192113 A1 Jul. 30, 2009

Related U.S. Application Data

(63) Continuation of application No. 10/569,927, filed as application No. PCT/EP2004/009599 on Aug. 27, 2004, now abandoned.

(60) Provisional application No. 60/498,514, filed on Aug. 28, 2003.

(51) Int. Cl.
*C07H 21/04* (2006.01)

(52) U.S. Cl. ..................................... 536/24.5

(58) Field of Classification Search .................. None
See application file for complete search history.

(56) References Cited

U.S. PATENT DOCUMENTS

| | | | |
|---|---|---|---|
| 5,670,633 A | 9/1997 | Cook et al. |
| 5,898,031 A | 4/1999 | Crooke et al. |
| 5,976,567 A | 11/1999 | Wheeler et al. |
| 5,998,203 A | 12/1999 | Matulic-Adamic et al. |
| 6,005,087 A | 12/1999 | Cook et al. |
| 6,033,909 A | 3/2000 | Uhlmann et al. |
| 6,107,094 A | 8/2000 | Crooke et al. |
| 6,211,349 B1 | 4/2001 | Dale et al. |
| 6,476,205 B1 | 11/2002 | Buhr et al. |
| 6,506,559 B1 | 1/2003 | Fire et al. |
| 6,531,584 B1 | 3/2003 | Cook et al. |
| 6,815,432 B2 | 11/2004 | Wheeler et al. |
| 6,858,225 B2 | 2/2005 | Semple et al. |
| 7,056,704 B2 | 6/2006 | Tuschl et al. |
| 7,078,196 B2 | 7/2006 | Tuschl et al. |
| 7,138,517 B2 | 11/2006 | Cook et al. |
| 7,432,249 B2 | 10/2008 | Crooke et al. |
| 7,432,250 B2 | 10/2008 | Crooke et al. |
| 7,629,321 B2 | 12/2009 | Crooke et al. |
| 2003/0143732 A1 | 7/2003 | Fosnaugh et al. |
| 2003/0148507 A1 | 8/2003 | Fosnaugh et al. |
| 2003/0175950 A1 | 9/2003 | McSwiggen |
| 2003/0190635 A1 | 10/2003 | McSwiggen |
| 2004/0019001 A1 | 1/2004 | McSwiggen |
| 2004/0152117 A1 | 8/2004 | Giordano et al. |
| 2004/0259247 A1 | 12/2004 | Tuschl et al. |
| 2005/0107325 A1 | 5/2005 | Manoharan et al. |
| 2005/0233329 A1 | 10/2005 | McSwiggen et al. |
| 2005/0261212 A1 | 11/2005 | McSwiggen |
| 2006/0063731 A1 | 3/2006 | Lewis et al. |
| 2007/0004667 A1 | 1/2007 | McSwiggen et al. |
| 2007/0032441 A1 | 2/2007 | McSwiggen et al. |
| 2009/0215880 A1 | 8/2009 | Li et al. |
| 2009/0247606 A1 | 10/2009 | McSwiggen et al. |
| 2009/0281164 A1 | 11/2009 | McSwiggen et al. |

FOREIGN PATENT DOCUMENTS

| | | |
|---|---|---|
| AU | 2002 326410 B2 | 2/2003 |
| AU | 03/216324 B2 | 9/2003 |
| AU | 04/266311 B2 | 3/2005 |
| DE | 100 80 167 B4 | 3/2008 |
| DE | 100 66 235 B4 | 4/2008 |
| EP | 0 552 766 B1 | 5/2002 |
| EP | 1 144 623 B1 | 8/2002 |
| EP | 1 229 134 A2 | 8/2002 |
| EP | 1389637 | 2/2004 |
| EP | 0 928 290 B1 | 3/2005 |
| EP | 1 214 945 B1 | 6/2005 |
| EP | 1 230 375 B1 | 7/2005 |
| EP | 1 627 061 B1 | 2/2006 |
| EP | 1 352 061 B1 | 5/2006 |
| EP | 1 407 044 B1 | 9/2007 |
| EP | 1 550 719 B1 | 12/2008 |

(Continued)

OTHER PUBLICATIONS

Czaudema et al., "Structural variations and stabilising modifications of synthetic siRNAs in mammalian cells" Nucleic Acids Research 31(11): 2705-2716 (Jun. 1, 2003).

(Continued)

*Primary Examiner* — Tracy Vivlemore
(74) *Attorney, Agent, or Firm* — Frank Wu (57) ABSTRACT

The present invention relates to double-stranded RNA compounds with at least one blunt end comprising at least one 3'-end of formula

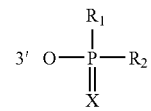

wherein
X is O or S
$R_1$ and $R_2$ are independently OH, $NH_2$, SH, alkyl, aryl, alkyl-aryl, aryl-alkyl, where alkyl, aryl, alkyl-aryl, aryl-alkyl can be substituted by additional heteroatoms and functional groups, preferably a heteroatom selected from the group of N, O, or S or a functional group selected from the group OH, $NH_2$, SH, carboxylic acid or ester;
or $R_1$ and $R_2$ may be of formula Y-Z where Y is O, N, S and Z is H, alkyl, aryl, alkyl-aryl, aryl-alkyl, where alkyl, aryl, alkyl-aryl, aryl-alkyl can be substituted by additional heteroatoms, preferably a heteroatom selected from the group of N, O, or S;
and wherein said double-stranded RNA mediates RNA interference.

10 Claims, 2 Drawing Sheets

FOREIGN PATENT DOCUMENTS

| | | | |
|---|---|---|---|
| EP | 1 309 726 B1 | 12/2009 | |
| JP | 4095895 B2 | 6/2008 | |
| WO | 02/096927 | 12/2002 | |
| WO | 03/070918 | 8/2003 | |
| WO | WO 03/070895 A2 | 8/2003 | |
| WO | 2004/015107 | 2/2004 | |
| WO | 2004/090105 | 10/2004 | |
| WO | 2004/092383 | 10/2004 | |
| WO | WO 2005/019453 A2 | 3/2005 | |
| WO | WO 2005/021749 A1 | 3/2005 | |
| WO | WO 2005/115481 A2 | 12/2005 | |
| WO | WO 2007/128477 A2 | 11/2007 | |

OTHER PUBLICATIONS

Hamada et al., "Effects of RNA Interference in Gene Expression (RNAI) in Cultured Mammalain Cells of Mismatches and the Introduction of Chemical Modifications at the 3'-Ends of SIRNAS" Antisense & Nucleic Acid Drug Development 12(5): 301-309 (Oct. 2002).

Chiu et al., "RNAi in Human Cells: Basic Structural and Functional Features of Small Interfering RNA" Molecular Cell 10: 549-561 (Sep. 2002).

Hamilton et al., "Two classes of short interfering RNA in RNA silencing" The EMBO Journal 21(17):4671-4679 (2002).

Lingel et al., "Structure and nucleic acid binding of the Drosophila Argonaute 2 PAZ domain" Letters to Nature 426:465-469 (Nov. 2003).

Seela et al., "Oligodeoxyribonucleotides containing 1,3-propanediol as nucleoside substitute" Nucleic Acid Research 15(7):3113-3129(1987).

Song et al., "The crystal structure of the Argonaute2 PAZ domain reveals an RNA binding motif in RNAi effector complexes" Nature Structural Biology 10(12):1026-1032 (Dec. 2003).

Takeshita et al., "Oligodeoxynucleotides Containing Synthetic Abasic Sites" The Journal of Biological Chemistry 262(21):10171-10179 (Jul. 25, 1987).

Yan et al., "Structure and conserved RNA binding of the PAZ domain" Letters to Nature 426:469-475 (Nov. 27, 2003).

Aubert et al; "Optimized Synthesis of Phosphorothioate Oligodeoxyribonucleotides Substituted With a 5'-Protected Thiol Function and a 3'-Amino Group"; Nucleic Acids Research 28(3):818-825 (2000).

Biessen et al; "Targeted delivery of oligodeoxynucleotides to parenchymal liver cells in vivo"; Biochem. J. 340:783-792 (1999).

Biessen et al; "Targeted Delivery of Antisense Oligonucleotides to Parenchymal Liver Cells in Vivo"; Methods in Enzymology 314:324-342 (1999).

Fennewald et al; "Inhibition of High Affinity Basic Fibroblast Growth Factor Binding by Oligonucleotides"; The Journal of Biological Chemistry 270(37):21718-21721 (1995).

Klysik et al; "A 15-Base Acridine-Conjugated Oligodeoxynucleotide Forms Triplex DNA with Its IL-2Rr Promoter Target with Greatly Improved Avidity"; Bioconjugate Chem. 8:318-326 (1997).

McShan et al; "Inhibition of Transcription of HIV-1 in Infected Human Cells by Oligodeoxynucleotides Designed to Form DNA Triple Helices"; The Journal of Biological Chemistry 267(8):5712-5721 (1992).

Nelson et al; "Bifunctional oligonucleotide probes synthesized using a novel CPG support are able to detect single base pair mutations"; Nucleic Acids Research 17(18):7187-7194 (1989).

Olejnik et al; "Photocleavable aminotag phosphoramidites for 5'-termini DNA/RNA labeling"; Nucleic Acids Research 26(15):3572-3576 (1998).

Rando et al; "Suppression of Human Immunodeficiency Virus Type 1 Activity in Vitro by Oligonucleotides Which Form Intramolecular Tetrads"; The Journal of Biological Chemistry 270(4):1754-1760 (1995).

Thomas et al; "Capping of bcr-abl Antisense Oligonucleotides Enhances Antiproliferative Activity Against Chronic Myeloid Leukemia Cell Lines"; Leukemia Research 18(6):401-408 (1994).

Beaucage et al; "The Functionalization of Oligonucleotides Via Phosphoramidite Derivatives"; Tetrahedron 49 (10):1925-1963 (1993).

Elbashir et al; "Functional anatomy of siRNAs for mediating efficient RNAi in Drosophila melanogaster embryo lysate"; The EMBO Journal 20(23):6877-6888 (2001).

Elbashir et al; "RNA interference is mediated by 21- and 22-nucleotide RNAs"; Genes & Development 15:188-200 (2001).

Guy-Caffey et al; "Novel Polyaminolipids Enhance the Cellular Uptake of Oligonucleotides"; The Journal of Biological Chemistry 270(52):31391-31396 (1995).

Igloi; "Nonradioactive Labeling of RNA"; Analytical Biochemistry 233:124-129 (1996).

Kim et al; "Inhibition of Ocular Angiogenesis by Sirna Targeting Vascular Endothelial Growth Factor Pathway Genes Therapeutic Strategy for Herpetic Stromal Keratitis" American Journal of Pathology, Philadelphia, PA, US, vol. 165, No. 6, Dec. 2004, pp. 2177-2185, XP009042137 ISSN: 0002-9440 the whole document.

Nelson et al; "A new and versatile reagent for incorporating multiple primary aliphatic amines into synthetic oligonucleotides"; Nucleic Acids Research 17(18):7179-7186 (1989).

Shen et al; "Suppression of ocular neovascularization with siRNA targeting VEGF receptor 1" Gene Therapy, Macmillan Press Ltd., Basingstoke, GB, vol. 13, No. 3, Sep. 29, 2005, pp. 225-234, the whole document.

Zendegui et al; "In vivo stability and kinetics of absorption and disposition of 3' phosphopropyl amine oligonucleotides"; Nucleic Acids Research 20(2):307-314 (1992).

Zhao et al; "Comparison of Cellular Binding and Uptake of Antisense Phosphodiester, Phosphorothioate, and Mixed Phosphorothioate and Methylphosphonate Oligonucleotides"; Antisense Research and Development 3:53-66 (1993).

Al-Anouti et al.; "Comparative Analysis of Antisense RNA, Double-Stranded RNA, and Delta Ribozyme-Mediated Gene Regulation in Toxoplasma gondii"; Antisense and Nucleic Acid Drug Development; 12:275-281 (2002).

Bass; "The short answer"; Nature—News and Views, RNA Interference; 411:428-429 (2001).

Beigelman et al.; "Chemical Modification of Hammerhead Ribozymes"; The Journal of Biological Chemistry; 270(43):25702-25708 (1995).

Braasch et al.; "Novel Antisense and Peptide Nucleic Acid Strategies for Controlling Gene"; Biochemistry—Current Topics; 41(14):4503-4510 (2002).

Braasch et al.; "RNA Interference in Mammalian Cells by Chemically-Modified RNA"; Biochemistry; 42:7967-7975 (2003).

Bramsen et al.; "A large-scale chemical modification screen identifies design rules to generate siRNAs with high activity, high stability and low toxicity"; Nucleic Acids Research; 37(9):2867-2881 (2009).

Bramsen et al.; "A large-scale chemical modification screen identifies design rules to generate siRNAs with high activity, high stability and low toxicity [Supplemental Figures]"; Nucleic Acids Research; 37(9):2867-2881 (2009).

Chiu et al; "Visualizing a Correlation between siRNA Localization, Cellular Uptake, and RNAi in Living Cells"; Chemistry & Biology; 11:1165-1175 (2004).

Chiu et al.; "siRNA function in RNAi: A chemical modification analysis"; RNA; 9:1034-1048 (2003).

Corey; "Chemical modification: the key to clinical application of RNA interference?"; The Journal of Clinical Investigation—Review Series; 117(12):3615-3622 (2007).

Crooke et al.; "Metabolism of Antisense Oligonucleotides in Rat Liver Homogenates"; The Journal of Pharmacology and Experimental Therapeutics; 292(1):140-149 (2000).

Deleavey et al.; "Chemical Modification of siRNA"; Current Protocols in Nucleic Acid Chemistry [Published by John Wiley & Sons, Inc.]; 39:16.3.1-16.3.22 (2009).

Dorsett et al.; "siRNAs: Applications in Functional Genomics and Potential As Therapeutics"; Nature Reviews—Drug Discovery; 3:318-329 (2004).

Elbashir et al.; "Duplexes of 21-nucleotide RNAs mediate RNA interference in cultured mammalian cells"; Nature; 411:494-498 (2001).

Hadwiger et al.; "Chemical modifications to achieve increased stability and sensitive detection of siRNA"; RNA Interference Technology—From Basic Science to Drug Development, Edited by Krishnarao Appasani, Published by Cambridge University Press; 14:194-206 (2005).

Harborth et al.; "Sequence, Chemical, and Structural Variation of Small Interfering RNAs and Short Hairpin RNAs and the Effect on Mammalian Gene Silencing"; Antisense and Nucleic Acid Drug Development; 13:83-105 (2003).

Hasan et al.; "VEGF antagonists"; Expert Opin. Biol. Ther.—Review; 1(4):703-718 (2001).

Kawasaki et al.; "World of small RNAs: from ribozymes to siRNA and miRNA"; Differentiation—Review; 72:58-64 (2004).

Kennerdell et al.; "Heritable gene silencing in Drosophila using double-stranded RNA"; Nature Biotechnology; 17:896-898 (2000).

Khan et al.; "Sustained Polymeric Delivery of Gene Silencing Antisense ODNs, siRNA, DNAzymes and Ribozymes: in Vitro and in Vivo Studies"; Journal of Drug Targeting; 12(6):393-404 (2004).

Kim et al; "Local and systemic delivery of VEGF siRNA using polyelectrolyte complex micelles for effective treatment of cancer"; Journal of Controlled Release; 129:107-116 (2008).

Kraynack et al.; "Small interfering RNAs containing full 2'-O-methylribonucleotide-modified sense strands display Argonaute2/eIF2C2-dependent activity"; RNA; 12:163-176 (2006).

Lipardi et al.; "RNAi as Random Degradative PCR: siRNA Primers Convert mRNA into dsRNAs that Are Degraded to Generate New siRNAs"; Cell; 107:297-307 (2001).

Miyagishi et al.; "Comparison of the Suppressive Effects of Antisense Oligonucleotides and siRNAs Directed Against the Same Targets in Mammalian Cells"; Antisense and Nucleic Acid Drug Development; 13:1-7 (2003).

Parrish et al.; "Functional Anatomy of a dsRNA Trigger: Differential Requirement for the Two Trigger Strands in RNA Interference"; Molecular Cell; 6:1077-1087 (2000).

Prakash et al.; "Positional Effect of Chemical Modifications on Short Interference RNA Activity in Mammalian Cells"; J. Med. Chem.; 48:4247-4253 (2005).

Schwarz et al; "Evidence that siRNAs Function as Guides, Not Primers, in the Drosophila and Human RNAi Pathways"; Molecular Cell; 10:537-548 (2002).

Shah et al.; "An ESI-MS method for characterization of native and modified oligonucleotides used for RNA interference and other biological applications"; Nature Protocols; 3(3):351-356 (2008).

Sioud; "Ribozymes and siRNAs: From Structure to Preclinical Applications"; HEP [Published by Springer-Verlag Berlin Heidelberg]; 173:223-242 (2006).

Takahashi et al.; "Synthesis and characterization of 2'-modified-4'-thioRNA: a comprehensive comparison of nuclease stability"; Nucleic Acids Research; 37(4):1353-1362 (2009).

Tavernarakis et al.; "Heritable and inducible genetic interference by double-stranded RNA encoded by transgenes"; Nature Genetics; 24:180-183 (2000).

Terrazas et al.; "RNA major groove modifications improve siRNA stability and biological activity"; Nucleic Acids Research; 37(2):346-353 (2009).

Ueno et al.; "Synthesis and properties of siRNAs containing 5'-amino-2',5'-dideoxy-2'alpha-fluororibonucleosides"; Tetrahedron; 64:11328-11334 (2008).

Ullu et al.; "RNA interference: advances and questions"; Phil. Trans. R. Soc. Lond. B; 357:65-70 (2002).

Wang et al.; "Subsection E Methods of RGS Protein Inhibition: [15] Ribozyme- and siRNA-Mediated Suppression of RGS-Containing RhoGEF Proteins"; Methods in Enzymology; 389:244-265 (2004).

Watts et al.; "Chemically modified siRNA: tools and applications"; Drug Discovery Today; 13(19/20):842-855 (2008).

Zhang et al.; "RNA interference in mammalian cells by siRNAs modified with morpholino nucleoside analogues"; Bioorganic & Medicinal Chemistry; 17:2441-2446 (2009).

SEQUENCE LISTING

```
<160> NUMBER OF SEQ ID NOS: 30

<210> SEQ ID NO 1
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (20)..(21)
<223> OTHER INFORMATION: 2'-methoxyethyl ribonucleoside,
      phosphorothioate link

<400> SEQUENCE: 1
acuccaucca gccgagugaa g                                             21

<210> SEQ ID NO 2
<211> LENGTH: 21
```

```
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (20)..(21)
<223> OTHER INFORMATION: 2'-methoxyethyl ribonucleoside,
      phosphorothioate link

<400> SEQUENCE: 2
ucacucggcu ggauggagut t                                          21

<210> SEQ ID NO 3
<211> LENGTH: 19
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (19)..(19)
<223> OTHER INFORMATION: hydroxypropylphosphodiester

<400> SEQUENCE: 3
acuccaucca gccgaguga                                             19

<210> SEQ ID NO 4
<211> LENGTH: 19
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (19)..(19)
<223> OTHER INFORMATION: hydroxypropylphosphodiester

<400> SEQUENCE: 4
ucacucggcu ggauggagu                                             19

<210> SEQ ID NO 5
<211> LENGTH: 19
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (19)..(19)
<223> OTHER INFORMATION: phosphate

<400> SEQUENCE: 5
acuccaucca gccgaguga                                             19

<210> SEQ ID NO 6
<211> LENGTH: 19
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (19)..(19)
<223> OTHER INFORMATION: phosphate

<400> SEQUENCE: 6
ucacucggcu ggauggagu                                             19

<210> SEQ ID NO 7
```

```
<211> LENGTH: 19
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (19)..(19)
<223> OTHER INFORMATION: abasic-abasic

<400> SEQUENCE: 7
acuccaucca gccgaguga                                               19

<210> SEQ ID NO 8
<211> LENGTH: 19
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (19)..(19)
<223> OTHER INFORMATION: abasic-abasic

<400> SEQUENCE: 8
ucacucggcu ggauggagu                                               19

<210> SEQ ID NO 9
<211> LENGTH: 21
<212> TYPE: DNA
<213> ORGANISM: Artificial
<220> FEATURE:
<223> OTHER INFORMATION: Oligonucleotide

<400> SEQUENCE: 9
ucgaaguacu cagcguaagt t                                            21

<210> SEQ ID NO 10
<211> LENGTH: 21
<212> TYPE: DNA
<213> ORGANISM: Artificial
<220> FEATURE:
<223> OTHER INFORMATION: Oligonucleotide

<400> SEQUENCE: 10
cuuacgcuga guacuucgat t                                            21

<210> SEQ ID NO 11
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (20)..(21)
<223> OTHER INFORMATION: 2'-methoxyethyl ribonucleoside

<400> SEQUENCE: 11
ggccauccac agucuucugg g                                            21

<210> SEQ ID NO 12
<211> LENGTH: 21
<212> TYPE: RNA
<213> ORGANISM: Artificial
<220> FEATURE:
<223> OTHER INFORMATION: Oligonucleotide

<400> SEQUENCE: 12
```
cagaagacug uggauggccu u                                          21

<210> SEQ ID NO 13
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (20)..(21)
<223> OTHER INFORMATION: 2'-methoxyethyl ribonucleoside

<400> SEQUENCE: 13
ggccagccac auucgucuug g                                          21

<210> SEQ ID NO 14
<211> LENGTH: 21
<212> TYPE: RNA
<213> ORGANISM: Artificial
<220> FEATURE:
<223> OTHER INFORMATION: Oligonucleotide

<400> SEQUENCE: 14
aagacgaaug uggcuggccu u                                          21

<210> SEQ ID NO 15
<211> LENGTH: 19
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (19)..(19)
<223> OTHER INFORMATION: hydroxypropylphosphodiester

<400> SEQUENCE: 15
ggccauccac agucuucug                                             19

<210> SEQ ID NO 16
<211> LENGTH: 19
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (19)..(19)
<223> OTHER INFORMATION: hydroxypropylphosphodiester

<400> SEQUENCE: 16
cagaagacug uggauggcc                                             19

<210> SEQ ID NO 17
<211> LENGTH: 19
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (19)..(19)
<223> OTHER INFORMATION: hydroxypropylphosphodiester

<400> SEQUENCE: 17
ggccagccac auucgucuu                                             19

<210> SEQ ID NO 18

```
<211> LENGTH: 19
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (19)..(19)
<223> OTHER INFORMATION: hydroxypropylphosphodiester

<400> SEQUENCE: 18
aagacgaaug uggcuggcc                                                    19

<210> SEQ ID NO 19
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (20)..(21)
<223> OTHER INFORMATION: 2'-methoxyethyl ribonucleoside

<400> SEQUENCE: 19
cauguaguug aggucaauga a                                                 21

<210> SEQ ID NO 20
<211> LENGTH: 21
<212> TYPE: RNA
<213> ORGANISM: Artificial
<220> FEATURE:
<223> OTHER INFORMATION: Oligonucleotide

<400> SEQUENCE: 20
cauugaccuc aacuacaugu u                                                 21

<210> SEQ ID NO 21
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (20)..(21)
<223> OTHER INFORMATION: 2'-methoxyethyl ribonucleoside

<400> SEQUENCE: 21
cauguagaug augcgauga a                                                  21

<210> SEQ ID NO 22
<211> LENGTH: 21
<212> TYPE: RNA
<213> ORGANISM: Artificial
<220> FEATURE:
<223> OTHER INFORMATION: Oligonucleotide

<400> SEQUENCE: 22
caucgacauc aucuacaugu u                                                 21

<210> SEQ ID NO 23
<211> LENGTH: 19
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (19)..(19)
```

-continued

```
<223> OTHER INFORMATION: hydroxypropylphosphodiester

<400> SEQUENCE: 23
cauguaguug aggucaaug                                           19

<210> SEQ ID NO 24
<211> LENGTH: 19
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (19)..(19)
<223> OTHER INFORMATION: hydroxypropylphosphodiester

<400> SEQUENCE: 24
cauugaccuc aacuacaug                                           19

<210> SEQ ID NO 25
<211> LENGTH: 19
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (19)..(19)
<223> OTHER INFORMATION: hydroxypropylphosphodiester

<400> SEQUENCE: 25
cauguagaug augucgaug                                           19

<210> SEQ ID NO 26
<211> LENGTH: 19
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (19)..(19)
<223> OTHER INFORMATION: hydroxypropylphosphodiester

<400> SEQUENCE: 26
caucgacauc aucuacaug                                           19

<210> SEQ ID NO 27
<211> LENGTH: 19
<212> TYPE: RNA
<213> ORGANISM: Artificial
<220> FEATURE:
<223> OTHER INFORMATION: Oligonucleotide

<400> SEQUENCE: 27
cauguagaug augucgaug                                           19

<210> SEQ ID NO 28
<211> LENGTH: 19
<212> TYPE: RNA
<213> ORGANISM: Artificial
<220> FEATURE:
<223> OTHER INFORMATION: Oligonucleotide

<400> SEQUENCE: 28
cauugaccuc aacuacaug                                           19

<210> SEQ ID NO 29
```

```
<211> LENGTH: 19
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (19)..(19)
<223> OTHER INFORMATION: phosphate

<400> SEQUENCE: 29
cauguagaug augucgaug                                                    19

<210> SEQ ID NO 30
<211> LENGTH: 19
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (19)..(19)
<223> OTHER INFORMATION: phosphate

<400> SEQUENCE: 30
cauugaccuc aacuacaug                                                    19
```

INTERFERING RNA DUPLEX HAVING BLUNT-ENDS AND 3'-MODIFICATIONS

RELATED APPLICATIONS

This application is a continuation of U.S. patent application Ser. No. 10/569,927, filed 28 Sep. 2006 now abandoned, which is a 371 application of PCT/EP04/09599 filed 27 Aug. 2004, which claims benefit to U.S. application 60/498514 filed 28 Aug. 2003, all of which are hereby incorporated by reference.

FIELD OF THE INVENTION

The invention relates to selective inhibition of target genes using double-stranded RNA and provides compounds useful for this purpose.

BACKGROUND OF THE INVENTION

Short RNA duplexes have been shown to be the effective guides that mediate RNA interference in many in vitro and in vivo models (Hamilton et al. 1999, Zamore et al., 2000, Caplen et al., 2001, Elbashir et al., 2001, Yang et al., 2000). Most commonly, synthetic siRNA duplexes are designed such as a stretch of 19 contiguous ribonucleotide base-pairs is flanked with 2-3 unpaired nucleotides at the 3'-end of each strand ("overhangs"). This 21-nt siRNA species has been found to be generated during DICER-mediated cleavage of long ds-RNA in mammalian and non-mammalian systems (Bernstein et al., 2001, Ketting et al., 2001). This particular 21-mer siRNA format has been firstly selected from a *drosophila melanogaster* model and then highlighted regarding its efficiency (Elbashir et al. 2001). Consequently, the major part of today's studies applying synthetic siRNAs as gene inhibitors is relying on this "Wildtype" 21-mer siRNA derivative. For the overhangs usually 2'-deoxynucleotides are used, notably for cost reasons but also with regard to a potential-protection against intracellular nuclease activity.

The present invention now provides a new and inventive format for double-stranded RNA ("dsRNA") mediating RNAi. The blunt-ended siRNAs in accordance with the present invention overcome disadvantages of the synthetic siRNAs with 3'-overhangs which are currently used in the art.

SUMMARY OF THE INVENTION

The present invention provides double-stranded RNA with at least one blunt end comprising at least one 3'-end of formula:

formula I wherein

X is O or S $R_1$ and $R_2$ are independently OH, $NH_2$, SH, alkyl, aryl, alkyl-aryl, aryl-alkyl, where alkyl, aryl, alkyl-aryl, aryl-alkyl can be substituted by additional heteroatoms and functional groups, preferably a heteroatom selected from the group of N, O, or S or a functional group selected from the group OH, $NH_2$, SH, carboxylic acid or ester;

Also, $R_1$ and $R_2$ may be of formula Y-Z where Y is O, N, S and Z is H, alkyl, aryl, alkyl-aryl, aryl-alkyl, where alkyl, aryl, alkyl-aryl, aryl-alkyl can be substituted by additional heteroatoms, preferably a heteroatom selected from the group of N, O, or S;

and wherein said double-stranded RNA mediates RNA interference.

DETAILED DESCRIPTION OF THE INVENTION

The present invention is based on the surprising finding that synthetic double-stranded RNA (dsRNA) molecules with at least one blunt end comprising a certain type of chemical modification efficiently mediate RNA interference. The dsRNAs according to the present invention are particularly useful for high-throughput approaches using siRNAs due to their simplified synthetic procedure, such as for instance the use of a universal solid support.

In one aspect, the present invention relates to double-stranded RNA with at least one blunt end comprising at least one 3'-end of the formula:

Formula I wherein

X is O or S $R_1$ and $R_2$ are independently OH, $NH_2$, SH, alkyl, aryl, alkyl-aryl, aryl-alkyl, where alkyl, aryl, alkyl-aryl, aryl-alkyl can be substituted by additional heteroatoms and functional groups, preferably a heteroatom selected from the group of N, O, or S or a functional group selected from the group OH, $NH_2$, SH, carboxylic acid or ester;

Also, $R_1$ and $R_2$ may be of formula Y-Z where Y is O, N, S and Z is H, alkyl, aryl, alkyl-aryl, aryl-alkyl, where alkyl, aryl, alkyl-aryl, aryl-alkyl can be substituted by additional heteroatoms, preferably a heteroatom selected from the group of N, O, or S;

and wherein said double-stranded RNA mediates RNA interference.

$R_1$ and $R_2$ may also form a cyclic structure, e.g. a carbocyclic or heterocyclic ring, the ring structure preferably having from 3 to 7 members.

In a preferred embodiment, Z is one or more a basic nucleoside, preferable ribonucleoside, moieties. The nucleoside moieties may be linked for instance by a phosphodiester or a phosphorothioate group.

In another preferred embodiment, $R_1$ is OH. In another preferred embodiment, $R_1$ and $R_2$ together comprise from 1 to 24 C-atoms more preferably from 1 to 12, or from 2 to 10 and most preferably from 1 to 8 or from 2 to 6. In another preferred embodiment, $R_1$ and $R_2$ are independently OH, lower alkyl, lower aryl, lower alkyl-aryl, lower aryl-alkyl, where lower alkyl, lower aryl, lower alkyl-aryl, lower aryl-alkyl can be substituted by additional heteroatoms and functional groups as defined above. In another preferred embodiment, $R_1$ and $R_2$ are not both OH.

The term "lower" in connection with organic radicals or compounds means a compound or radical which may be branched or unbranched with up to and including 7 carbon atoms, preferably 1-4 carbon atoms. Lower alkyl represents, for example, methyl, ethyl, n-propyl, isopropyl, n-butyl, sec-butyl, tert-butyl, n-pentyl and branched pentyl, n-hexyl and branched hexyl.

In related aspect, the present invention relates to double-stranded RNA with at least one blunt end comprising at least one 3'-end of the formula:

formula II wherein $R_3$ is OH, $NH_2$, SH, alkyl, aryl, alkyl-aryl, aryl-alkyl, where alkyl, aryl, alkyl-aryl, aryl-alkyl can be substituted by additional heteroatoms, preferably a heteroatom selected from the group of N, O, or S, and $R_4$ is independently alkyl, aryl, alkyl-aryl, aryl-alkyl, where alkyl, aryl, alkyl-aryl, aryl-alkyl can be substituted by additional heteroatoms, preferably a heteroatom selected from the group of N, O, or S or a functional group selected from the group OH, $NH_2$, SH, carboxylic acid or ester, and wherein said double-stranded RNA mediates RNA interference. $R_3$ and $R_4$ may also form a cyclic structure, e.g. a carbocyclic or heterocyclic ring, the ring structure preferably having from 3 to 7 members.

$R_3$ and $R_4$ may further comprise additional heteroatoms, preferably a heteroatom selected from the group of N, O, or S.

In preferred embodiment, $R_3$ is OH. In another preferred embodiment, $R_3$ and $R_4$, respectively, together comprise from 1 to 24 C-atoms more preferably from 1 to 12, or from 2 to 10 and most preferably from 1 to 8 or from 2 to 6. In another preferred embodiment, $R_3$ is lower alkyl, lower aryl, lower alkyl-aryl, lower aryl-alkyl, where lower alkyl, lower aryl, lower alkyl-aryl, lower aryl-alkyl can be substituted by additional heteroatoms and functional groups as defined above and $R_4$ is, independently lower alkyl, lower aryl, lower alkyl-aryl, lower aryl-alkyl, where lower alkyl, lower aryl, lower alkyl-aryl, lower aryl-alkyl can be substituted by additional heteroatoms and functional groups as defined above.

In a related aspect, the present invention relates to double-stranded RNA with at least one blunt end comprising at least one 3'-end of the formula:

formula III wherein $R_5$ and $R_6$ are the same or different and are H, alkyl, aryl, alkyl-aryl, aryl-alkyl, where alkyl, aryl, alkyl-aryl, aryl-alkyl can be substituted by additional heteroatoms, preferably a heteroatom selected from the group of N, O or S, or a functional group selected from the group OH, $NH_2$, SH, carboxylic acid or ester wherein said double-stranded RNA mediates RNA interference. $R_5$ and $R_6$ may also form a cyclic structure, e.g. a carbocyclic or heterocyclic ring, the ring structure preferably having from 3 to 7 members.

$R_5$ and $R_6$ may further comprise additional heteroatoms, preferably a heteroatom selected from the group of N, O or S.

In preferred embodiment, $R_5$ and $R_6$, respectively, together comprise from 1 to 24 C-atoms more preferably from 1 to 12 or from 2 to 10 and most preferably from 1 to 6 or from 2 to 6. In another preferred embodiment, $R_5$ and $R_6$ are independently lower alkyl, lower aryl, lower alkyl-aryl, lower aryl-alkyl, where lower alkyl, lower aryl, lower alkyl-aryl, lower aryl-alkyl can be substituted by additional heteroatoms and functional groups as defined above.

In another embodiment $R_5$ and $R_6$ are not both H.

The RNA molecules of the present invention will have at least at least one strand comprising a 3'-ends of the formula I, II or III. Preferably, both strands of the double-stranded RNA comprise 3'-ends comprising a group of the formula I, II or III. The RNA molecules of the present invention will further have at least one blunt end, preferably two blunt ends. In a particularly preferred embodiment, the RNA molecules of the present invention are blunt ended on both sides and both ends comprise 3'-ends of the formula I, II or III.

The RNA molecules in accordance with the present invention will have at least a partially double-stranded character In a preferred embodiment, they are fully double-stranded. They may be composed of two separate strands, but may also be composed of one strand forming a hairpin loop. In a particularly preferred embodiment, the RNA molecules of the present invention are composed of two separate strands which are fully double-stranded comprising at least one, preferably two, blunt ends.

The RNA molecules according to the present invention mediate RNA interference ("RNAi"). The term "RNAi" is well known in the art and is commonly understood to mean the inhibition of one or more target genes in a cell by dsRNA with a region which is complementary to the target gene. Various assays are known in the art to test dsRNA for its ability to mediate RNAi (see for instance Elbashir et al., Methods 26 (2002), 199-213). The effect of the dsRNA according to the present invention on gene expression will typically result in expression of the target gene being inhibited by at least 10%, 33%, 50%, 90%, 95% or 99% when compared to a cell not treated with the RNA molecules according to the present invention.

The RNA molecules in accordance with the present invention comprise a double-stranded region which is substantially identical to a region of the mRNA of the target gene. Particularly preferred is a region with 100% identity to the corresponding sequence of the target gene. However, the region may also contain one or two mismatches as compared to the corresponding region of the target gene. The present invention includes RNA molecules which target more than one gene. In a preferred embodiment, the RNA molecules of the present invention specifically target one given gene. In order to only target the desired mRNA, the siRNA reagent should have 100% homology to the target mRNA and at least 2 mismatched nucleotides to all other genes present in the cell or organism. Methods to analyze and identify dsRNAs with sufficient sequence identity in order to effectively inhibit expression of a specific target sequence are known in the art.

Sequence identity may be optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BEST-FIT software program using default parameters (e.g., University of Wisconsin Genetic Computing Group). Another factor affecting the efficiency of the RNAi reagent is the target region of the target gene. The region of a target gene effective for inhibition by the RNAi reagent may be determined by experimentation. Most preferred mRNA target region would be the coding region. Also preferred are untranslated regions, particularly the 3'-UTR, splice junctions. For instance, transfection assays as described in Elbashir S. M. et al, 2001 EMBO J., 20, 6877-6888 may be performed for this purpose. A number of other suitable assays and methods exist in the art which are well known to a person skilled in the art.

The length of the complementary region of the RNA molecules in accordance with the present invention is preferably from 10 to 100 nucleotides, more preferably 15 to 50 nucleotides, even more preferably 17 to 30 nucleotides and most preferably 19 to 25 nucleotides. In a particularly preferred embodiment the RNA molecules in accordance with the present invention consist of short dsRNA molecules having a length from 15 to 50 nucleotides, more preferably 17 to 30 nucleotides and most preferably 19 to 25 nucleotides.

The 3' end of the dsRNA according to the present invention confer a high in vivo stability in serum or in growth medium for cell cultures. Thus, the dsRNA according to the present invention does not require additional stabilization against nuclease degradation as is common in the art, for instance, by adding a 3'-overhang of 2 or 3 deoxynucleotides. However, the dsRNA according to the present invention may also contain at least one modified or non-natural ribonucleotide. Preferred modifications are include, but are not limited to modifications at the 2' position of the sugar moiety, such as for instance 2'-O-(2-methoxyethyl) or 2'-MOE) (Martin et al., Helv. Chim. Acta, 1995, 78, 486-504) i.e., an alkoxyalkoxy group. Other preferred modifications include backbone modifications including, but not limited to, replacing the phosphoester group connecting adjacent ribonucleotides with for instance phosphorothioates, chiral phosphorothioates or phosphorodithioates. Methods for the synthesis of modified or non-natural ribonucleotide are well known and readily available to those of skill in the art.

The dsRNA molecules may be prepared by a method comprising the steps:
(i) synthesizing the two RNA strands each using, for instance, TOM chemistry as illustrated in Example 1. Other methods to synthesis RNA strands are readily apparent to a person of skill in the art. The reaction may be carried out in solution or, preferably, on solid phase or by using polymer supported reagents.
(ii) combining the synthesized RNA strands under conditions, wherein a dsRNA molecule is formed, which is capable of mediating RNA.

In another aspect, the present invention provides methods for the inhibition of a target gene comprising introducing into a cell dsRNA according to the present invention, which is capable of inhibiting at least one target gene by RNAi. Also, more than one species of dsRNA, which are each specific for another target region, may be introduce into a cell at the same time or sequentially. The dsRNA according to the present invention can be introduced into a cell by various standard methods in genetic engineering, including physical methods, for example, simple diffusion, by injection of a solution containing the nucleic acid, bombardment by particles covered by the nucleic acid, soaking the cell or organism in a solution of the nucleic acid, lipofection or electroporation of cell membranes in the presence of the nucleic acid. A particularly preferred method for delivering nucleic acids is the use of lipofection. The cells are subsequently maintained under conditions under which RNAi occurs. It will be readily apparent to the skilled artisan under what conditions a given cell line is maintained in order that RNAi occurs. This method for the inhibition of a target gene can be used therapeutically (e.g. for knocking down a gene overexpressed in a particular disease) or for research (e.g. examine function of a gene or validate targets for drug discovery). In a preferred embodiment, the gene function is completely eliminated by this method, i.e. knock-out cells for a particular gene can be generated by this method.

The cell may be a plant or an animal cell. In a preferred embodiment, the cell is a mammalian cell, more preferably a human cell. The type and source of the cell is not critical for the invention, thus the invention includes for instance cells from the inner cell mass, extraembryonic ectoderm or embryonic stem cells, totipotent or pluripotent, dividing or non-dividing, parenchyma or epithelium, immortalized or transformed, or the like. The cell may be a stem cell or a differentiated cell. Cell types that are differentiated include without limitation adipocytes, fibroblasts, myocytes, cardiomyocytes, endothelium, dendritic cells, neurons, glia, mast cells, blood cells and leukocytes (e.g., erythrocytes, megakaryotes, lymphocytes, such as B, T and natural killer cells, macrophages, neutrophils, eosinophils, basophils, platelets, granulocytes), epithelial cells, keratinocytes, chondrocytes, osteoblasts, osteoclasts, hepatocytes, and cells of the endocrine or exocrine glands, as well as sensory cells.

In another aspect, dsRNA according to the present invention is used for the identification of gene function in an organism wherein the activity of a target gene of previously unknown function is inhibited. Instead of the time consuming and laborious isolation of mutants by traditional genetic screening, functional genomics would envision determining the function of uncharacterized genes by employing the dsRNA according to the present invention to reduce the amount and/or alter the timing of target gene activity. The dsRNA according to the present invention could be used in determining potential targets for pharmaceuticals, understanding normal and pathological events associated with development, determining signaling pathways responsible for postnatal development/aging, and the like. The increasing speed of acquiring nucleotide sequence information from genomic and expressed gene sources, including the human genome, can be coupled with the invention to determine gene function in mammalian systems, in particular in human cell culture systems.

The ease with which RNA can be introduced into an intact mammalian cell containing the target gene allows the method for the inhibition of a target gene according to the present invention to be used in high throughput screening (HTS). For example, solutions containing RNA molecules according to the present invention that are capable of inhibiting a given target gene can be placed into individual wells positioned on a microtiter plate as an ordered array. Subsequently, intact cells in each well can be assayed for any changes or modifications in behavior or development due to inhibition of target gene activity or by proteomic, genomics and standard molecular biology techniques. Thus, the function of the target gene can be assayed from the effects it has on the cell when gene activity is inhibited.

The present invention is not limited to any type of target gene or nucleotide sequence. For example, the target gene can be a cellular gene, an endogenous gene, a pathogen-associated gene, a viral gene or an oncogene. The following classes of possible target genes are listed for illustrative purposes only and are not to be interpreted as limiting: transcription factors and developmental genes (e.g., adhesion molecules, cyclin kinase inhibitors, Wnt family members, Pax family members, Winged helix family members, Hox family members, cytokines/lymphokines and their receptors, growth/differentiation factors and their receptors, neurotransmitters and their receptors); oncogenes (e.g., ABLI, BCLI, BCL2, BCL6, CBFA2, CBL, CSFIR, ERBA, ERBB, ERBB2, ETSI, ETV6, FGR, FOS, FYN, HCR, HRAS, JUN, KRAS, LCK, LYN, MDM2, MLL, MYB, MYC, MYCLI, MYCN, NRAS, PIMI, PML, RET, SKP2, SRC, TALI, TCL3, and YES); tumor suppressor genes (e.g., APC, BRAI, BRCA2, CTMP, MADH4, MCC, NF1, NF2, RB1, TP53, and WTI); and enzymes (e.g., ACP desaturases and hydroxylases, ADP-glucose pyrophorylases, ATPases, alcohol dehydrogenases, amylases, amyloglucosidases, catalases, cyclooxygenases, decarboxylases, dextrinases, DNA and RNA polymerases, galactosidases, glucose oxidases, GTPases, helicases, integrases, insulinases, invertases, isomerases, kinases, lactases, lipases, lipoxygenases, lysozymes, peroxidases, phosphatases, phospholipases, phosphorylases, proteinases and peptidases, recombinases, reverse transcriptases, telomerase, including RNA and/or protein components, and topoisomerases).

A gene derived from any pathogen may be targeted for inhibition. For example, the gene could cause immunosuppression of the host directly or be essential for replication of the pathogen, transmission of the pathogen, or maintenance of the infection. Cells at risk for infection by a pathogen or already infected cells, such as cells infected by human immunodeficiency virus (HIV) infections, influenza infections, malaria, hepatitis, plasmodium, cytomegalovirus, herpes simplex virus, and foot and mouth disease virus may be targeted for treatment by introduction of RNA according to the invention. The target gene might be a pathogen or host gene responsible for entry of a pathogen into its host, drug metabolism by the pathogen or host, replication or integration of the pathogen's genome, establishment or spread of an infection in the host, or assembly of the next generation of pathogen. Methods of prophylaxis (i.e., prevention of decreased risk of infection), as well as reduction in the frequency or severity of symptoms associated with infection, can be envisioned.

In another aspect, the invention further provides a method for identifying and/or characterizing pharmacological agents acting on at least one target protein comprising:
contacting a eukaryotic cell, preferably a mammalian cell, more preferably a human cell capable of expressing at least one endogenous gene coding for the protein(s) of interest with (a) at least one dsRNA molecule according to the present invention, which is capable of inhibiting the expression of the gene(s) encoding the protein(s) of interest and
(b) a test substance or a collection of test substances wherein pharmacological properties of said test substance or said collection are to be identified and/or characterized. The cells might be concomitantly or sequentially contacted with the dsRNA and the compound(s) to be tested, the order in which the cells are contacted with the dsRNA and the compound(s) is of not crucial. In a preferred embodiment, the cells further comprise at least one exogeneous nucleic acid coding for variant or mutated form of the protein(s) of interest, wherein the expression of said exogenous nucleic acid is less inhibited by said dsRNA.

In another aspect, the invention also provides a kit comprising reagents for inhibiting expression of a target gene in a cell, wherein said kit comprises dsRNA according to the present invention. The kit comprises at least one of the reagents necessary to carry out the in vitro or in vivo introduction of the dsRNA according to the present invention to test samples or subjects. In a preferred embodiment, such kits also comprise instructions detailing the procedures by which the kit components are to be used.

Another aspect of the present invention provides pharmaceutical compositions and formulations which include dsRNA according to the present invention which is capable of inhibiting at least one target gene by RNAi. The pharmaceutical compositions may also contain more than one species of dsRNA which are each specific for another target region. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers. The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1-50 mM histidine, 0.1%-2% sucrose, and 2-7% mannitol, at a pH range of 4.5 to 5.5, that is combined with buffer prior to use.

The determination of an effective dose is well within the capability of those skilled in the art. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between toxic and therapeutic effects is the therapeutic index, and it can be expressed as the ratio, LD50/ED50. Pharmaceutical compositions that exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration. Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

The following examples are intended to illustrate, but not further limit, the invention.

EXAMPLES

Example 1

Procedures for Synthesis of Solid Support LM-17

3-[Bis-(4-methoxy-phenyl)-phenyl-methoxy]-propan-1-ol (LM-14)

To a solution of 1,3-propanediol (20 ml, 268 mmol) in absolute pyridine (20 ml) under an argon atmosphere was added 4,4'-dimethoxytriphenylchloromethane (1.87 g, 5.4 mmol). After stirring at room temperature for 10 minutes, the mixture was poured onto an ice/water mixture and extracted with ethyl acetate (twice). The combined organic phases were washed with water (twice) and brine, dried over sodium sulfate, filtered and concentrated. The obtained brown liquid was purified by column chromatography (silica gel, eluent: ethyl acetate/hexane=1:2) yielding 1.56 g (77%) of LM-14 as a slightly yellow oil.

Succinic Acid mono-{3-[bis-(4-methoxy-phenyl)-phenyl-methoxy]-propyl}ester (LM-15)

To a solution of LM-14 (250 mg, 0.69 mmol) in absolute pyridine (5 ml) under an argon atmosphere was added N,N-dimethylaminopyridine (45 mg, 0.37 mmol). After addition of succinic anhydride (57 mg, 0.57 mmol) the mixture was stirred at room temperature overnight. The reaction mixture was diluted with ethyl acetate and washed with brine (3 times). The organic phase was dried over sodium sulfate, filtered, concentrated to yield crude LM-15 (536 mg) which was used without further purification in the subsequent step.

Solid Support LM-17

To a solution of the crude LM-15 (0.69 mmol) in a mixture of absolute DMF (5 ml) was added pyridine (0.13 ml), 4-nitrophenol (143 mg, 1.0 mmol) and N,N-d dicyclohexylcarbodiimide (DCC: 156 mg, 0.76 mmol) under an argon atmosphere. The yellow solution was stirred at room temperature for two days, after which a yellow suspension had formed. After filtration over celite, amino-derivatised polystyrene (457 mg) was added to the filtrate. Triethylamine (0.046 ml) was added and the mixture was shaken using a mechanical bottle shaker for 24 hours. The mixture was filtered and the solid support was washed twice each with DMF (5 ml), methanol (5 ml) and diethyl ether (5 ml) to give LM-17 (453 mg). Quantitation (absorption at 498 nm) of trityl groups released upon treatment with 0.1 ml of a solution of p-toluenesulfonic acid (1.9 g) in acetonitrile (100 ml) revealed a loading of 14 µmol/g.

Example 2

1. Synthesis of Oligoribonucleotides (siRNA's)

Modified synthetic oligoribonucleotides described in this invention can be prepared using standard TOM-phosphoramidite chemistry on ABI394 or Expedite/Moss Synthesizers (Applied Biosystems). Phosphoramidites are dissolved in acetonitrile at 0.05 M concentration (0.2M on OligoPilot II), coupling is made by activation of phosphoramidites by a 0.2 M solution of benzimidazolium triflate in acetonitrile. Coupling times are usually comprised between 3-6 minutes. A first capping is made using standard capping reagents. Oxidation is made by a 0.1 M iodine solution in THF/Pyridine/Water (77:20:3) or 0.5M t-butylhydroxyperoxide (Fluka) in dichloromethane for two minutes. A second capping is performed after oxidation. Oligonucleotide growing chains are detritylated for the next coupling by 2% dichloroacetic acid in dichloromethane or dichloroethane. After completion of the sequences the support-bound compounds are cleaved and deprotected as "Trityl-on" by a Methylamine solution (41% aqueous methylamine/33% ethanolic methylamine 1:1 v/v) at 35° C. for 6 h. Resulting suspensions are lyophilised to dryness. 2'-O-silyl groups are removed upon treatment with 1M tetrabutylammonium fluoride 10 min at 50° C. and 6 h at 35° C. The obtained crude solutions are directly purified by RP-HPLC. The purified detritylated compounds are analysed by Electrospray Mass spectrometry and Capillary Gel Electrophoresis and quantified by UV according to their extinction coefficient at 260 nM. Oligonucleotide sequences are listed in Table 1:

| NickName | Target | Antisense strand | Sense strand | SEQ ID NO |
|---|---|---|---|---|
| siRNA 8646 | p2x3 | ACU CCA UCC AGC CGA GUG Aasg | UCA CUC GGC UGG AUG GAG Utst | 1, 2 |
| C3-8646 | p2x3 | ACU CCA UCC AGC CGA GUG A-C3 | UCA CUC GGC UGG AUG GAG U-C3 | 3, 4 |
| phosphate-8646 | p2x3 | ACU CCA UCC AGC CGA GUG A-p | UCA CUC GGC UGG AUG GAG U-p | 5, 6 |
| abasic-8646 | p2x3 | ACU CCA UCC AGC CGA GUG A-ab-ab | UCA CUC GGC UGG AUG GAG Uab-ab | 7, 8 |
| sIRNA 8549 | luc | UCG AAG UAC UCA GCG UAA GdTdT | CUU ACG CUG AGU ACU UCG AdTdT | 9, 10 |
| siRNA-10557 | GAPDH | GGC CAU CCA CAG UCU UCU Ggg | CAG AAG ACU GUG GAU GGC CUU | 11, 12 |
| MM siRNA-10559 | GAPDH | GGC CAG CCA CAU UCG UCU Ugg | AAG ACG AAU GUG GCU GGC CUU | 13, 14 |
| C3-10569 | GAPDH | GGC CAU CCA CAG UCU UCU G-C3 | CAG AAG ACU GUG GAU GGC C-C3 | 15, 16 |
| MM C3-10571 | GAPDH | GGC CAG CCA CAU UCG UCU U-C3 | AAG ACG AAU GUG GCU GGC C-C3 | 17, 18 |
| siRNA2 | hGAPDH | CAU GUA GUU GAG GUC AAU Gaa | CAU UGA CCU CAA CUA CAU GUU | 19, 20 |
| siRNA2 MM | hGAPDH | CAU GUA GAU GAU GUC GAU Gaa | CAU CGA CAU CAU CUA CAU GUU | 21, 22 |
| C3-siRNA2 | hGAPDH | CAU GUA GUU GAG GUC AAU G-C3 | CAU UGA CCU CAA CUA CAU G-C3 | 23, 24 |
| C3-siRNA2 MM | hGAPDH | CAU GUA GAU GAU GUC GAU G-C3 | CAU CGA CAU CAU CUA CAU G-C3 | 25, 26 |
| OH-siRNA | hGAPDH | CAU GUA GAU GAU GUC GAU G | CAU UGA CCU CAA CUA CAU G | 27, 28 |
| P2-siRNA | hGAPDH | CAU GUA GAU GAU GUC GAU G-p | CAU UGA CCU CAA CUA CAU G-p | 29, 30 |

N: RNA, n: 2'-methoxyethyl ribonucleoside, dN: deoxyribonucleoside, ab: abasic ribonucleoside, p: phosphate, s: phosphorothioate, C3: hydroxypropylphosphodiester

Example 3

3.1 Materials and Methods

Materials: Oligofectamine and other cell culture reagents are obtained from Life Technologies, GibcoBRL, now Invitrogen, Gaithersburg, Md.). JetPEI is purchased from Polyplus-Transfection (Illkirch, France).

Cell lines: Stably transfected Chinese hamster ovary cells (CHO-K1) (ATCC CCL61, American Type Culture Collection, Rockville, Md.) expressing recombinant rat $P2X_3$ are generated as described (Hemmings et al., NAR 31 (2003), 2117-2126). CHO cells are cultured in minimal essential medium (MEM-α) supplemented with 10% (v/v) FBS, 2 mM glutamine in a 5% $CO_2$-humidified chamber. HeLa cells are cultured in Dubelco's modified essential medium (DMEM 41965) supplemented with 10% (v/v) FBS, 2 mM glutamine in a 5% $CO_2$-humidifed chamber.

Oligonucleotide synthesis: Oligoribonucleotides are purchased at Qiagen or synthesized using TOM-phosphoramidite chemistry, as described by the manufacturer (Qiagen) and purified by RP-HPLC. 3'-hydroxypropylphosphate oligoribonucleotides are synthesized on solid support LM-17 (loading: 14 µmol/g). Oligonucleotide chain elongation, cleavage from the support, deprotection and purification are identical to that 21-mer oligoribonucleotides having two deoxynucleotides as 3'-overhangs.

Purity is assessed by capillary gel electrophoresis. Quantification is carried out by UV according to the extinction coefficient at 260 nM. Annealing of double-stranded RNA (dsRNA) is performed as described elsewhere (Elbashir et al., Methods 26 (2002), 199-213). Oligonucleotide sequences that are used in this report are listed in Table 1 and are characterized by electrospray mass spectroscopy.

Cell transfection: Cationic lipid-oligonucleotide (Oligofectamine) and polymer-oligonucleotide (jetPEI) mixtures are prepared immediately prior to transfection as previously described. Eighteen hours before transfection, $4 \times 10^4$ cells are plated into 24-well plates in a volume of 0.5 ml MEM-α for CHO cells or 0.5 ml DMEM for HeLa cells (both supplemented with 10% (v/v) FBS, 2 mM glutamine) per well. Prior to the transfection, growth medium is removed from the cells and replaced with 500 µl of OptiMEM and 100 µl of the transfecting reagent/oligonucleotide mixture. Plates are incubated at 37° in a humidified 5% CO2 incubator. After 4 hrs, 60 µl of FBS are added to each well, and the incubation was prolonged for 20 h.

RNA harvesting and Real-Time quantitative PCR mRNA analysis: Total RNA is isolated 24 h after oligonucleotide transfection with the RNeasy 96 kit (Qiagen, Chatsworth, Calif.) according to the manufacturer's protocol. The RNA samples are mixed with reagents from the Reverse Transcriptase Q-PCR mastermix kit (Eurogentec) and run according to the included protocol.

3.2 Blunt Ended siRNA Activity

A CHO cell-line expressing the rat $P2X_3$ purino-receptor is used to compare the relative activity of different mRNA inhibitors such as first and second generation oligonucleotides (ASO) as well as short interfering RNAs. Use of linear PEI as "universal" transfection reagent allows to perform head-to-head comparisons between these various gene expression inhibitors. The siRNA sequence was selected from an optimal ASO sequence previously characterized (Dorn et al., Antisense & Nucleic Acid Drug Development 11 (2001): 165-174), is designed to target the P2X3 coding sequence and has been shown to efficiently and selectively down-regulate P2X3 expression at the molecular level, as demonstrated by Q-RT-PCR, immunodetection and functional assay. As positive control, we use the siRNA sequence having two target-complementary 2'-MOE modified overhangs, linked together via a phosphorothioate internucleosidic bond. We then synthesize the corresponding 19-mer blunt-ended siRNA so that after ammonia mediated cleavage from the solid support, the released compound sustains a hydroxypropylphosphate (hpp) group on the 3'-position of its last ribonucleotide.

As an intermediate between the 21-mer siRNA (two complementary overhangs) and the blunt-ended 19-mer, a sequence homologous 21-nt siRNA with two abasic nucleoside overhangs is also synthesized. Such non-nucleosidic overhangs allows us to assess whether one of the steps involved in the RNAi pathway, and more particularly during the unwinding of the duplex, would absolutely require a 3'-elongation on siRNA.

Figure 1:
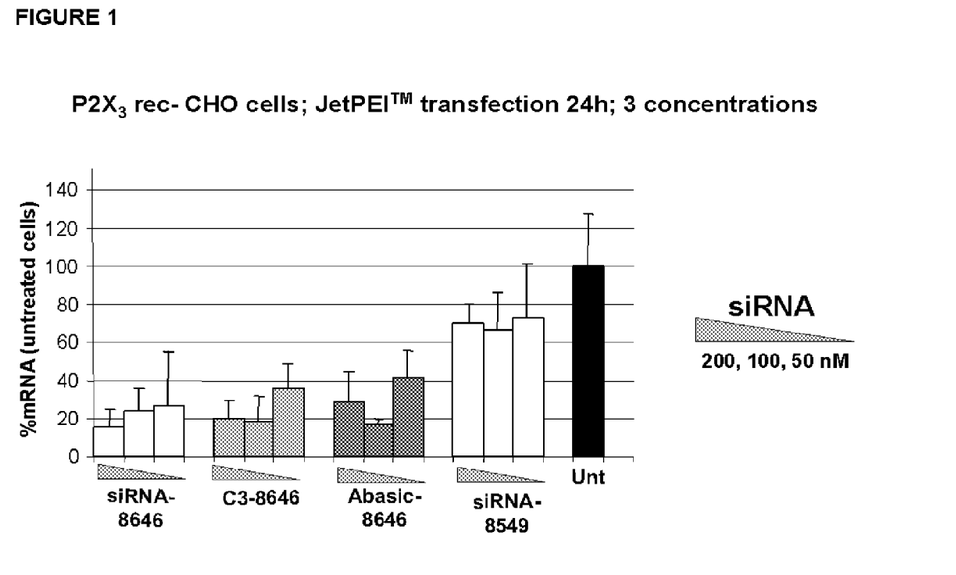
FIG. 1 shows the relative activity of different mRNA inhibitors in a CHO cell-line expressing the rat $P2X_3$ purinoreceptor.

The siRNAs are transfected into CHO cells using JetPEI at a N/P ratio of 5. mRNA levels are assessed by RT-Q-PCR 24 hours after transfection. As shown in FIG. 1, a decrease in the GAPDH mRNA level is detected in CHO cells with comparable level of down-regulation for all three compounds. The blunt-ended 19 bp siRNA having a 3'-hydroxypropylphosphate ribonucleotide shows the same efficacy in inhibiting $P2X_3$ mRNA as the "wild-type" 21-mer siRNA.

Figure 2:
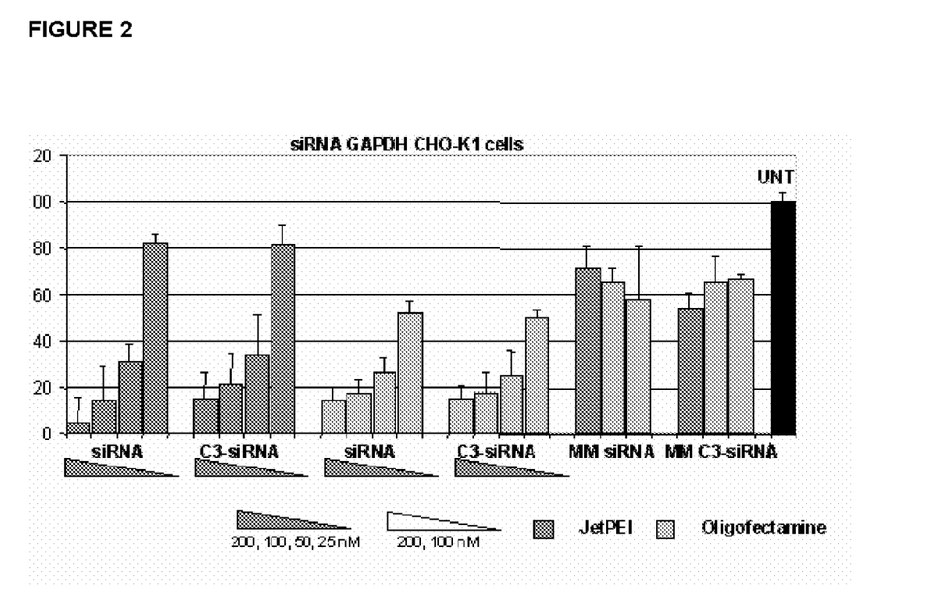
FIG. 2 shows the down-regulation in the GAPDH mRNA level detected when siRNAs were transfected into CHO cells.

We now apply a similar format modification to siRNA targeting an endogenous gene and design a siRNA sequence targeting the Chinese hamster GAPDH mRNA in a way that it is also specific and fully homolog to the human GAPDH gene. After transfection into CHO cells of the 21-mer siRNA (2 deoxyribonucleotidic overhangs) and the blunt-ended 3'-hydroxypropylphosphate siRNA (19-mer) at concentrations ranging from 25 to 200 nM, RT-Q-PCR analysis of the chinese hamster GAPDH mRNA level shows an equivalent mRNA down-regulation for the two compounds, although down-regulation is slightly more pronounced in the case of a "wild-type" siRNA at high concentrations. However, when transfected at the same concentrations with the cationic lipid Oligofectamine, both compounds showed exactly the same mRNA inhibition, as shown in FIG. 2.

Taken together, these data shows that modification or absence of oligonucleotidic overhangs on the 3'-end of siRNAs are in CHO cells not critical regarding their interfering activity.

3.3 Blunt-Ended siRNA Activity in Human Cells

Figure 3:
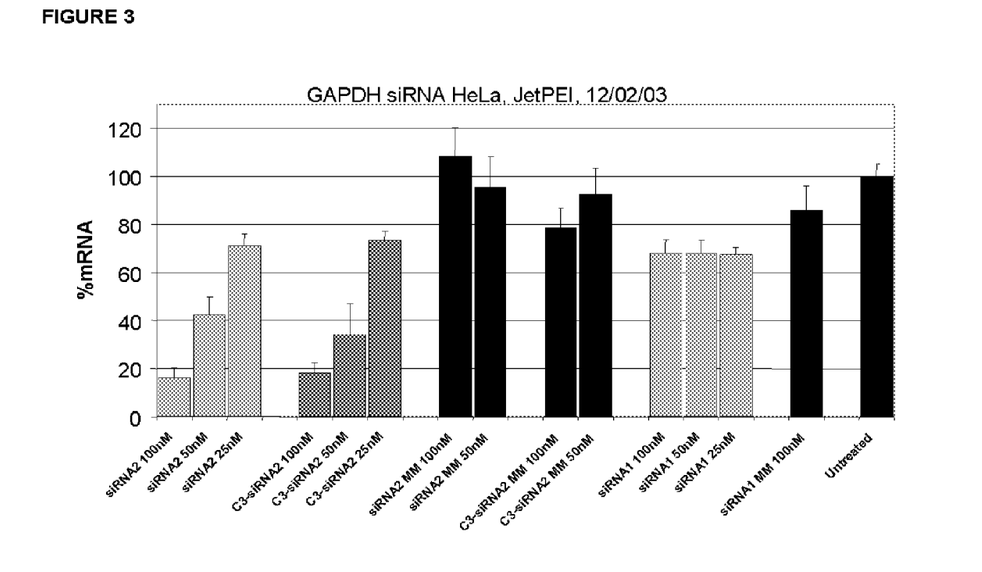
FIG. 3 shows that both blunt-ended and wild-type siRNAs silence the human GAPDH in HeLa cells with the same level of target down-regulation.

To validate this first result in human cells, siRNA sequence targeting the human GAPDH mRNA open reading frame are designed. Both blunt-ended and wild-type siRNAs silence the human GAPDH in HeLa cells with the same level of target down-regulation (FIG. 3).

3.4 3' End Functional Requirements of Blunt-Ended siRNAs

Having shown in two different mammalian cell-lines and against different targets that depletion of the overhangs does not impair the silencing activity of the resulting blunt-ended siRNAs, we also evaluate whether the 3'-ribonucleotidic position on the first 3'-ribonucleotide of a blunt-ended siRNA would require a specific chemical moiety to be optimal in the silencing process.

Figure 4:
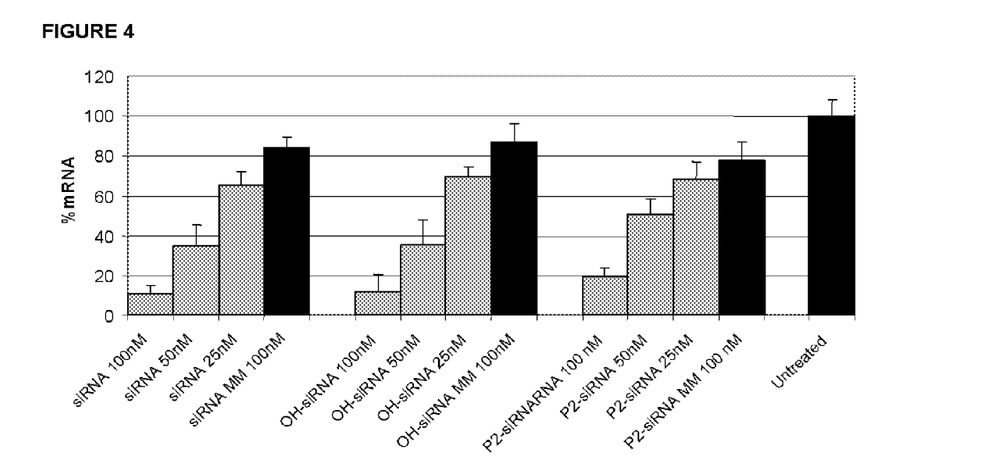
FIG. 4 shows that both blunt-ended 3'-hydroxy and 3'-phosphate siRNAs lead to a similar level of targeted GAPDH mRNA down-regulation in HeLa cells as the wild-type 21-mer siRNA.

As shown in FIG. 4, both blunt-ended 3'-hydroxy and 3'-phosphate siRNAs lead to a similar level of targeted GAPDH mRNA down-regulation in HeLa cells as the wild-type 21-mer siRNA, with a high selectivity as compared to the three nt mismatch controls.

---

The invention claimed is:

1. A double-stranded RNA with at least one blunt end, wherein the double-stranded RNA comprises at least one 3'-end, wherein the 3'-end is hydroxypropylphosphodiester, and wherein the 3'-end confers on the double-stranded RNA stability in serum or in growth medium for cell cultures, and wherein the double-stranded RNA is capable of inhibiting at least one target gene by RNA interference.

2. The double-stranded RNA of claim 1, wherein the double-stranded RNA comprises a stretch of 19 contiguous ribonucleotide base-pairs.

3. The double-stranded RNA of claim 1, wherein the length of the double-stranded RNA is 19 base-pairs.

4. The double-stranded RNA of claim 1, wherein the double-stranded RNA comprises two blunt ends.

5. The double-stranded RNA of claim 1, wherein the double-stranded RNA comprises a stretch of 19 contiguous ribonucleotide base-pairs, and the double-stranded RNA comprises two blunt ends.

6. The double-stranded RNA of claim 1, wherein the length of the double-stranded RNA is 19 base-pairs, and the double-stranded RNA comprises two blunt ends.

7. The double-stranded RNA of claim 1, wherein the double-stranded RNA comprises a stretch of 19 contiguous ribonucleotide base-pairs, and the double-stranded RNA comprises two 3' ends, wherein each of the two 3' ends is hydroxypropylphosphodiester.

8. The double-stranded RNA of claim 1, wherein the length of the double-stranded RNA is 19 base-pairs, and the double-stranded RNA comprises two 3' ends, wherein each of the two 3' ends is hydroxypropylphosphodiester.

9. The double-stranded RNA of claim 1, wherein the double-stranded RNA comprises a stretch of 19 contiguous ribonucleotide base-pairs, and the double-stranded RNA comprises two blunt ends, and the double-stranded RNA comprises two 3' ends, wherein each of the two 3' ends is hydroxypropylphosphodiester.

10. The double-stranded RNA of claim 1, wherein the length of the double-stranded RNA is 19 base-pairs, and the double-stranded RNA comprises two blunt ends, and the double-stranded RNA comprises two 3' ends, wherein each of the two 3' ends is hydroxypropylphosphodiester.

* * * * *